United States Patent [19]

Kijima et al.

[11] Patent Number: 4,880,745

[45] Date of Patent: Nov. 14, 1989

[54] *PSEUDOMONAS GLADIOLI* AND A PROCESS FOR BIOLOGICALLY CONTROLLING FUSARIUM DISEASES USING *PSEUDOMONAS GLADIOLI* PV. GLADIOLI

[75] Inventors: Toshio Kijima, Tochigi; Tokuya Tezuka, Utsunomiya; Yoji Doi, Tokyo; Shuiichi Yamashita, Tokyo; Shigetoh Namba, Tokyo; Tsutomu Arie, Hino, all of Japan

[73] Assignee: Tochigi Prefecture, Tochigi Prefecture, Japan

[21] Appl. No.: 12,649

[22] Filed: Feb. 9, 1987

[30] Foreign Application Priority Data

Aug. 9, 1986 [JP] Japan .................... 61-187575

[51] Int. Cl.[4] ............... C12R 1/38; A01N 63/00; A61K 37/00
[52] U.S. Cl. ..................... 435/253.3; 71/6; 71/9; 424/93; 435/243; 435/254; 435/874; 435/929
[58] Field of Search .............. 435/243, 253, 254, 874, 435/929, 253.3; 424/93; 71/6, 9

[56] References Cited

U.S. PATENT DOCUMENTS 4,588,584 5/1986 Lumsden et al. ............... 424/93
4,642,131 2/1987 Hoitink ........................ 435/850
4,714,614 12/1987 Scher ........................... 424/93

Primary Examiner—Robert A. Wax
Attorney, Agent, or Firm—Wenderoth, Lind & Ponack

[57] ABSTRACT

A new *Pseudomonas gladioli* having the identifying characteristics of Bikohken-kin No. 8805 has been discovered. The microorganism is a new bacteria separated from a bulb and roots of Miltonia. For separation, the bulb and roots of Miltonia are ground in a 1% solution of peptone followed by a streak culture on a bouillon agar at 25° C. for 48–96 hours, and the colonies thus grown are isolated. This microorganism is inoculated into a bulb and roots of a plant selected from the group consisting of Welsh onion, sorgo, oats and maize. The plants inoculated with the grown microorganisms are grown together within the radius of rhizosphere of a plant to be protected (or companion or mixed crop) for further multiplication of *Pseudomonas gladioli* M-2196 in order to control soil borne plant diseases caused by *Fusarium oxysporum*. Very strong antibacterial activity on *Fusarium oxysporum, Rhizoctonia solani, Verticillum dahliae, Corynebacterium michiganese* pv. *michiganese, Sclerotium cepivorum* etc. is observed.

2 Claims, No Drawings

PSEUDOMONAS GLADIOLI AND A PROCESS FOR BIOLOGICALLY CONTROLLING FUSARIUM DISEASES USING PSEUDOMONAS GLADIOLI PV. GLADIOLI

BACKGROUND OF INVENTION

1. Field of Invention

This invention relates to a new *Pseudomonas gladioli* and a process for biologically controlling Fusarium diseases caused by *Fusarium oxysporum* using *Pseudomonas gladioli* pv. gladioli.

2. Description of the Prior Art

Soil borne plant diseases such as Fusarium wilt, Fusarium root rot etc. are caused by *Fusarium oxysporum*, *Rhizoctonia solani*, Rhizoctonia rot, etc.

A soil disease is conventionally considered one of the malignant diseases, and once a plant is infected with the soil borne diseases, it is almost impossible to control it, usually causing annihilation of the neighboring plants as well.

Various searches for new soil microorganisms which have antibacterial activity on the aforementioned plant diseases have been made, but no soil microorganisms having strong antibacterial activity have been discovered.

Miltonia is widely cultivated in Tochigi Prefecture in Japan. The present inventors discovered a new microorganism which belongs to *Pseudomonas gladioli* and exhibits strong antibacterial activity on *Fusarium oxysporum*, *Rhizoctonia solani* etc.

As a result of further investigation, it has been found that when a Welsh onion (*Allium fistulosum* L.) is inoculated with *Pseudomonas gladioli*, it grows rapidly in the soil. On the basis of this discovery, a process for biologically controlling plant diseases has been developed. That is to say, the plant diseases caused by *Fusarium oxysporum, Rhizoctonia solani, Corticium rolfsil, Verticillium dahliae, Sclerotium cepivorum* or *Corynebacterium michiganese* pv. michganese can be controlled by the process of this invention.

More particularly, the plants inoculated with *Pseudomonas gladioli* are grown together with a plant such as a bottle gourd (*Lagenaria sinceraria* Standl. var. hispida HARA) in the same field.

SUMMARY OF THE INVENTION

A principal object of this invention is to provide a *Pseudomonas gladioli* and a process for biologically controlling Fusarium diseases using *Pseudomonas gladioli*, whereby a soil microorganism, *Pseudomonas gladioli*, is inoculated into a plant for multiplication, and the inoculated plant is grown together near the root of the plant to be protected in order to biologically control plant diseases caused by *Fusarium oxysporum*.

DESCRIPTION OF THE INVENTION

As described in the foregoing paragraph, the microorganism of this invention is a new bacteria separated from a bulb and a root of Miltonia which is a kind of orchid. For isolation of a single cell, the bulb and roots of the Miltonia are ground in a 1% solution of peptone followed by streak culture on a bouillon agar at 25° C. for to 48–96 hours, and the colonies thus grown are isolated.

It has been found that the microorganism has the following mycological properties, and it is understood that the microorganism belongs to *Pseudomonas gladioli*, but it is identified as a variant of *Pseudomonas gladioli* for the reasons mentioned in detail hereinafter.

Accordingly, the present microorganism was named *Pseudomonas gladioli* M-2196, and it has been deposited with the Industrial Technical Institute of Microorganisms of the Government Agency of Industrial Science and Technology, the deposit number of which is Bikohken-kin No. 8805.

The mycological properties of this microorganism are as follows.

| (a) Morphology of new *Pseudomonas gladioli*. | |
|---|---|
| Shape and size of cell | rod of 1.0~1.2 × 1.6~2.2μ |
| Polymorphism | no |
| Adherent condition of flagellum | 1~2 of polar flagella |
| Spore | negative |
| Gram's stain | negative |
| Acido-fast | negative |
| Accumulation of poly-β-butyric acid granule | negative |

| (b) Growth condition on various culture media. | |
|---|---|
| Bouillon agar plate culture | Excellent growth was observed, producing smooth, circular, entire, semi-hyaline, and polished yellowish colonies. |
| Bouillon agar slant culture | Excellent growth was observed. |
| Bouillon broth culture | Homogeneously turbid formation of membraneous cover on the surface. |
| Stick culture on a bouillon gelatin | Liquefied. |
| Litmus.milk | Digested to produce alkaline, but litmus was not reduced. |

| (c) Physiological properties. | |
|---|---|
| (1) General physiological properties. | |
| Reduction of nitrate | positive |
| Reaction of denitrification | negative |
| MR test | negative |
| VP test | negative |
| Production of indole | negative |
| Production of hydrogen sulfide | negative |
| Hydrolysis of starch | negative |
| Utilization of inorganic nitrogen source | positive |
| Production of fluorescence pigment | negative |
| Production of water soluble pigment | positive |
| Urease | negative |
| Oxidase | weak positive |
| Catalase | positive |
| Growth range temperature | 8~41° C. |
| Attitude on oxygen | aerobic |
| O-F test | oxidative |

| (2) Production of acid and gas from sacchrides. | | |
|---|---|---|
| | acid | gas |
| L-arabinose | positive | negative |
| D-arabinose | positive | negative |
| D-xylose | positive | negative |
| G-glucose | positive | negative |
| D-mannose | positive | negative |
| D-fructose | positive | negative |
| D-galactose | positive | negative |
| Maltose | positive | negative |
| Saccharose | positive | negative |
| Milk sugar | positive | negative |
| Trehalose | positive | negative |
| D-sorbitol | positive | negative |
| D-mannitol | positive | negative |
| Inositol | positive | negative |
| Glycerol | positive | negative |
| Starch | negative | negative |

| (3) Other physiological properties. | |
|---|---|
| Utilization of alcohol | negative |

| -continued | |
|---|---|
| Hydrolysis of aesculin | positive |
| Utilization of hippuric acid | positive |
| Utilization of malonic acid | positive |
| Hydrolysis of alginic acid | negative |
| Decarboxylation reaction of lysin | weak positive |
| Growth in 5% sodium chloride | negative |
| Lipase | positive |
| Lecithinase | positive |

(3) Utilization test.

| | | | |
|---|---|---|---|
| Saccharin acid | positive | Palmitic acid | weak positive |
| Levulinic acid | positive | Myristic acid | positive |
| Mesaconic acid | negative | Sorbic acid | positive |
| Acetic acid | positive | Maleic acid | positive |
| Citric acid | positive | Anthranilic acid | positive |
| Formic acid | positive | Isovaleric acid | negative |
| Fumaric acid | positive | n-capric acid | positive |
| Malic acid | positive | Decane acid | positive |
| Oxalic acid | negative | Glutaric acid | positive |
| Propionic acid | positive | Valine | positive |
| Succinic acid | positive | L-citrulline | positive |
| Lactic acid | positive | β-alanine | positive |
| D-tartaric acid | weak positive | | |
| | | P—aminobenzoic acid | negative |
| Benzoic acid | negative | Betaine | positive |
| Gluconic acid | positive | Folic acid | negative |
| Alginic acid | positive | L-ornithine | positive |
| Pantothenic acid | positive | n-heptanic acid | positive |
| Aspartic acid | positive | Butyric acid | positive |
| L-glutamic acid | positive | D-galacturonic acid | galacturonic positive |

Drawing upon Bergey's Manual of Systematic Bacteriology (1st Edition) for the properties mentioned in the foregoing paragraphs, it has proved that the microorganism of this invention is a Gram-negative rod which grows aerobically excellently on the bouillon agar and its oxidase activity is positive so that the present microorganism belongs to Pseudomonas genus. As closely allied species, there exist *Pseudomonas caryophylli* and *Pseudomonas cepacia*.

The present microorganism, however, hydrolyzes arginine, respires nitric acid, liquefies gelatin, and utilizes pimelic acid, suberic acid, levulinic acid, meso-hydroxybenzoic acid, strepcin, amylamine, isoleucine and nicotinic acid so that it is different from *Pseudomonas caryophylli*.

The size of bacteria of *Pseudomonas caryophylli* is $0.8 \sim 1.0 \times 1.6 \sim 3.2 \mu$, while that of the present microorganism is $1.0 \sim 1.2 \times 1.6 \sim 2.2 \mu$. At the same time, the latter reduces nitrate, and utilizes maltose, raffinose, spermine, butylamine, triptamine, D-tartaric acid and isovaleric acid, thus differentiating it from *Pseodomonas cepacia*. Consequently, it is reasonable to classify the present microorganism into *Pseudomonas gladioli*.

Strictly speaking, the microorganism of this invention is significantly different from *Pseudomonas gladioli* in the following points, namely, contrary to *Pseudomonas gladioli*, this microorganism utilizes pimelic acid, suberic acid, levulinic acid, meso-hydroxybenzoic acid, strepcin, butanediol and amylamine. In addition, the present microorganism does not utilize mesaconic acid, but *Pseudomonas gladioli* utilizes it.

It has been understood that the microorganism may not be classified into *Pseudomonas gladioli* as it is, but it may be identified as a variant thereof, thus naming it "*Pseudomonas gladioli* M-2196".

Having studied its mycological property, it has been proved that the present microorganism has excellent antibacterial activity on *Fusarium oxysporum*, *Rhizoctonia solani* etc.

The mycological properties of new *Pseudomonas gladioli* are shown in the following paragraph.

TABLE (Test result showing antibacterial property on various) bacteria.

| Plant | Disease | Pathogenic bacteria | Antibacterial activity |
|---|---|---|---|
| Cymbidum spp. | Fusarium rot | F. oxysporum | +++ |
| Kidney bean (Phaseolus) | root rot | F. solani | ++ |
| Radish (Raphanus sativas L.) | yellows | F. oxysporum f. sp. raphani | ++ |
| Phyro-cerus (Zygocactus truncactus) | basal stem rot | F. oxysporum | +++ |
| Watermelon (Citrullus vulgaris SCHARAD.) | Fusarium wilt | F. oxysporom f. sp. | |
| Dendrobium (Dendrobium spp.) | stem rot | F. oxysporum | ++ |
| Cerus (Zygocactus spp.) | basal stem rot | F. oxysporum | ++ |
| Cyclamen (Cyclamen persicum MILL.) | Fusarium wilt | F. oxysporum f. sp. cyclaminis | ++ |
| Soybean [Glycine max (L.) MERRIL] | Fusarium blight | F. oxysporum sp. tracheiphilum | ++ |
| Easter cactus (Zygocactus spp.) | basal stem rot | F. oxysporum | ++ |
| Japanese iris (Iris Kaempferi PLANCHON) | rot | F. oxysporum | ++ |
| Chinese chive (Allium tubersum ROTTL.) | basal stem rot | F. oxysporum | ++ |

TABLE-continued (Test result showing antibacterial property on various) bacteria.

| Plant | Disease | Pathogenic bacteria | Antibacterial activity |
|---|---|---|---|
| Common stock (*Mathiola icana* R. SR.) | Fusarium wilt | *F. oxysporum* | ++ |
| Cucumber (*Cucumio sativa* L.) | Fusarium rot | *F. oxysporum* f. sp. *cucumerinum* | ++ |
| Konnyaku (*Amorphophallus Kojac* C. KOCH.) | rot | *F. solani* | +++ |
| Scallion (*Allium Chinese* G. DON) | dry rot | *F. oxysporum* f. sp. *allii* | +++ |
| Strawberry (*Fragaria x ananassa* Duch. EHRN.) | Fusarium wilt | *F. oxysporum* f. sp. *fragariae* | ++ |
| Tomato (*Lycopersicum esculentum* MILL.) | root and stem rot | *F. oxysporum* f. sp. *lycopersici* | ++ |
| bottle gourd (*Lagenaria siceraria* STANDLEY var. *hispida* HARA) | Fusarium wilt rot | *F. oxysporum* f. sp. *lagenariae* | +++ |
| Garlic (*Allium sativa* L.) | bulb rot | *F. oxysporum* | +++ |
| Lily (*Lilium* spp.) | bulb rot | *F. oxysporum* f. sp. *lilli* | + |
| Asparagus (*Asparagus officinalis* L.) | Fusarium blight | *F. oxysporum asparagi* | + |
| Onion (*Allium cepa* L.) | Fusarium basal rot | *F. oxysporum* f. sp. *cepae* | + |
| Chinese chive (*Allium tuberosum* ROTTI.) | southern blight | *Corticium rolfsil* | +++ |
| Cucumber (*Cucumio sativas* L.) | damping off | *Rhizoctonia solani* | +++ |
| Tomato (*Lycopersicum esculentum* Mill.) | Verticillium wilt | *Verticillium dahliae* | +++ |
| Tomato | bacterial canker | *Corynebacterium michiganese* pv. *michiganese* | +++ |
| Chinese chive | white rot | *Sclerotium cepivorum* | ++ |

From the foregoing table, very strong antibacterial activity on *Fusarium oxysporum, Rhizoctonia solani, Verticillum dahliae, Corynebacterium michiganese* pv. michiganese, *Sclerotium cepivorum* was observed.

Taking notice of this excellent antibacterial activity, the present inventors tried to control or exterminate the plant diseases caused by the foregoing pathogens, but it has been proved that when the present microorganism is introduced into the soil as it is, it does not grow well, and it is impossible to use its antibacterial activity on the foregoing plant diseases.

Having carried out further investigation, it has found that a Welsh onion (*Allium fistulosum* L.), sorgo, (*vulgare* PERS.), oat (*Avena sativa* L.), maize (*Zea mays* L.) etc. have an affinity for the present microorganism, and that when these plants inoculated with the grown microorganisms are planted together with the control plant, the microorganisms are further grown in the soil, and finally a process for biologically controlling the foregoing plant diseases has been developed.

More particularly, thr grown microorganisms of this invention are liquefied or pulverized through vacuum drying, inoculated into a seedling or seed either of a Welsh onion, sorgo, oat or maize each having an affinity for the microorganism, and the plant inoculated with the microorganisms is grown together with the control plant in the same field.

"Companion crops" means to grow two crops together in the same field or in a rhizosphere of the control plant, one of the crops, and often both benefiting from the presence of the other, and their roots are crossed together.

For example, (a) A Welsh onion is grown together within the rhizosphere of about 1.5 m of a bottle gourd, the former having the same rhizosphere as that of the latter;

(b) A Chinese chive is planted together within the radius of rhizosphere of about 0.5 m of a tomato, the former having the radius of rhizosphere of about 0.5 m;

(c) An oat having a radius of rhizosphere of about 0.5 m is planted within a radius of rhizosphere of 0.3 m of a Konnyaku.

It has been confirmed experimentally that in case the plant such as a bottle gourd is infected with the pathogenic microorganisms, the present microorganisms in the roots of a Welsh onion multiply extensively with an affinity for such plants, the grown microorganisms exhibit strong antibacterial activity on the pathogenic bacteria in the adjacent portion of the control plant, decompose and control them completely.

As is clear from the foregoing table showing the antibacterial activity, the present microorganism shows excellent antibacterial activity on Fusarium disease caused by *Fusarium oxysporum, Rhizoctonia solani, Corticium rolfsil, Verticillium dahliae, Sclerotium cepivorum, Corynebacterium michiganess* pv. michiganense etc. Practically, it is good for rot, root rot, yellow dwarf, stem rot, wilt, Verticillium wilt, damping-off, dry rot, blight, southern blight, surface rot, white rot etc.

As mentioned in the foregoing paragraphs, a soil disease has been conventionally considered a fatal disease, and once a plant is infected with any of the soil diseases, it is almost impossible to control the fungi, annihilating not only the infected plant, but also the neighboring plants. Such plant diseases cause much damage to vegetable farmers.

Several examples of this invention will be described in the following paragraphs.

EXAMPLE 1

The present microorganism was cultured on a bouillon agar at 25° C. for 72 hours, and bulbs both of a Welsh onion and a Chinese chive were immersed into its culture solution for inoculation. Subsequently, the Welsh onion and Chinese chive were grown together around 20 cm from the foot of a bottle gourd when the latter was set.

| Control of stem rot of a bottle gourd | |
|---|---|
| Process for treatment | Rate of diseased plant |
| Not treated | 100% |
| A Welsh onion inoculated with the present microorganism was grown together near the root of a bottle gourd in the same field. | 0% |
| A Chinese chive inoculated with the present microorganism was grown together near the root of a bottle gourd in the same field. | 0% |

EXAMPLE 2

A Chinese chive was inoculated with the present microorganism under the same condition as that of EXAMPLE 1, and the Chinese chive was grown together around 20 cm from the root of a tomato when the latter was set.

| Control of root and stem rot of a tomato | |
|---|---|
| Process for treatment | Rate of diseased plants |
| Not treated | 61.7% |
| A Chinese chive inoculated with the present microorganism was grown together near the root of a tomato in the same field. | 35.0% |

EXAMPLE 3

A Chinese chive inoculated with the microorganism of this invention was grown together around 20 cm from the root of a strawberry when the latter was set.

| Control of strawberry Fusarium wilt | |
|---|---|
| Process for treatment | Degree of browning of vascular bundle |
| Not treated. | +++ |
| A Chinese chive inoculated with the present microorganism was grown together near the root of a strawberry in the same field. | — |
| A Welsh onion inoculated with the present microorganism was grown together near the root of a strawberry. | — |

While in the foregoing specification embodiments of the invention have been set forth in considerable detail for the purposes of making a complete disclosure of the invention, it will be apparent to those of ordinary skill in the art that numerous changes may be made in such details without departing from the spirit and principles of the invention.

What is claimed is:

1. A biologically pure culture of the microorganism *Pseudomonas gladioli* for biologically controlling plant disease caused by *Fusarium oxysporum*, having the identifying characteristics of Bikohken-kin No.8805, said culture having antifungal activity and also being capable of growing in a bulb and/or roots of at least a plant selected from the group consisting of Welsh onion, sorgo, oats and maize.

2. A process for biologically controlling plant disease caused by *Fusarium oxysporum* using *Pseudomonas gladioli* pv. gladioli, which comprises
   a step of inoculating *Pseudomonas gladioli* M-2196 into a bulb and/or roots of at least a plant selected from the group consisting of Welsh onion, sorgo, oats and maize;
   a step of planting the inoculated plants together within the radius of rhizosphere of a plant to be protected for further multiplication of *Pseudomonas gladioli* M-2196; and
   a step of controlling soil borne plant disease by means of antifungal activity against *Fusarium oxysporum*.

* * * * *